United States Patent [19]

Chiccarelli

[11] 4,219,668

[45] Aug. 26, 1980

[54] 4-HYDROXY,4-BIPHENYLBUTYRIC ACID

[75] Inventor: Fortunato S. Chiccarelli, New City, N.Y.

[73] Assignee: American Cyanamid Company, Stamford, Conn.

[21] Appl. No.: 54,741

[22] Filed: Jul. 5, 1979

[51] Int. Cl.² .............................................. C07C 69/76
[52] U.S. Cl. .................................... 562/469; 424/308; 562/463; 562/492
[58] Field of Search ......................................... 562/469

[56] References Cited

U.S. PATENT DOCUMENTS

| 3,754,021 | 8/1973 | Shen | 562/469 |
| 3,859,338 | 1/1975 | Engel et al. | 562/469 |
| 3,859,363 | 1/1975 | Teufel et al. | 562/469 |
| 3,867,434 | 2/1978 | Diamond et al. | 562/469 |
| 3,867,435 | 2/1975 | Diamond et al. | 562/469 |
| 4,021,479 | 5/1977 | Seeger et al. | 562/469 |

FOREIGN PATENT DOCUMENTS 2329037 12/1974 Fed. Rep. of Germany ........... 562/469

OTHER PUBLICATIONS

Chem. Abstr., vol. 78, 1973, 3966r.

Primary Examiner—Paul J. Killos
Attorney, Agent, or Firm—Thomas M. Saunders

[57] ABSTRACT

Compounds of metabolites of 3-(4-biphenylylcarbonyl)-propionic acid useful as anti-inflammatory and anti-platelet aggregation agents.

7 Claims, No Drawings

4-HYDROXY,4-BIPHENYLBUTYRIC ACID

BACKGROUND OF THE INVENTION

This invention is concerned with the preparation and use of antithrombotic and anti-inflammatory drugs. Some prior examples of related compounds will now be considered. U.S. Pat. No. 3,966,978 to Ellenbogen et al. discloses the use of 4-biphenylacetic acid in the amelioration of blood platelet aggregation. U.S. Pat. No. 3,784,701 to Tomcufcik et al. discloses a group of anti-inflammatory drugs, substituted benzoylpropionic acids, including a biphenyl which is a starting material of some of the compounds of the invention.

U.S. Pat. No. 3,966,960 to Ellenbogen et al. is to the use of 3-(4-biphenylcarbonyl)propionic acid as an inhibitor of platelet aggregation. U.S. Pat. No. 3,784,704 to Cohen et al. describes the use and preparation of 4-biphenylacetic acid in the amelioration of pain.

U.S. Pat. No. 3,969,402 to Adams et al. discloses the preparation and use of 2-(hydroxy substituted-4-biphenylyl)propionic acids as anti-inflammatory agents.

British Pat. No. 1,390,091 describes the preparation and use of 5-(4-biphenylyl)-2-hydro-2-(3H)-furanone. The activity of this compound is indicated as "antiphlogistic" and inhibitory toward "the aggregation of thromocytes".

Finally, an article by H. Yoshizawa, Y. Tada, T. Naruke and M. Mizumura; Basic Pharmacology and Therapeutics, 2, No. 11, Dec. 5, 1974, pp. 31–40, describes 3-(4-biphenylylcarbonyl)propionic acid and derivatives.

SUMMARY OF THE INVENTION

This invention is concerned with compounds of the formula:

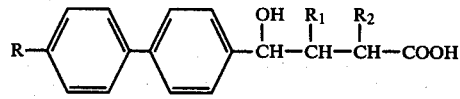

wherein R, $R_1$ and $R_2$ are each selected from the group consisting of hydrogen and hydroxy, said formula being intended to include both the erythro and threo configurations. The compound wherein R, $R_1$ and $R_2$ are all hydrogen is disclosed in Mizumura (above).

Specifically, the new compounds of this invention are:

γ,4'-Dihydroxy-4-biphenylbutyric acid
β,γ-Dihydroxy-threo-4-biphenylbutyric acid*
β,γ-Dihydroxy-erythro-4-biphenylbutyric acid*
α,γ-Dihydroxy-erythro-4-biphenylbutyric acid
α,γ-Dihydroxy-threo-4-biphenylbutyric acid
*Disclosed in the racemic form only in Mizumura.

This invention is further directed to methods of treating inflammation and platelet aggregation, by the administration of compounds of the formula:

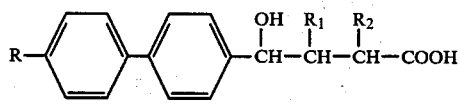

wherein R, $R_1$ and $R_2$ are each selected from the group comprising hydrogen and hydroxy.

Specifically, these compounds include the aforementioned plus γ-hydroxy-4-biphenylbutyric acid, which has been described in Chemical Abstracts 78, 3966r (1973).

DESCRIPTION OF THE INVENTION

γ-hydroxy-4-biphenylbutyric acid may be prepared by treating 3-(4-biphenylylcarbonyl)propionic acid with sodium borohydride in an alkaline medium and then acidifying the reaction mixture.

γ,4-dihydroxy-4-biphenylbutyric acid may be prepared by treating p-methoxybiphenyl with succinic anhydride in nitrobenzene. The mixture is treated with aluminum chloride at reduced temperature. The solid is dissolved in aqueous base with heat, chilled to reprecipitate and acidified giving 4'-methoxy-γ-oxo-4-biphenylbutyric acid. This intermediate is refluxed with hydrogen bromide for several hours, diluted with water and cooled. The precipitate is 4'-hydroxy-γ-oxo-biphenylbutyric acid. This intermediate is treated with sodium borohydride in an alkaline medium and then acidified giving the desired product.

β,γ-hydroxy-threo-4-biphenylbutyric acid may be prepared by treating 3-(4-biphenylylcarbonyl)propionic acid with bromine in methylene chloride giving β-bromo-γ-4-biphenylbutyric acid. This intermediate is treated with sodium borohydride in alkaline medium and acidified giving cis-5-(4-biphenylyl)dihydro-4-hydroxy-2(3H)-furanone. This intermediate is treated with base in ethanol and then acidified giving the desired product.

β,γ-hydroxy-erythro-4-biphenylbutyric acid is produced by the same process as the threo derivative except that the trans-5-(4-biphenylyl)dihydro-4-hydroxy-2(3H)-furanone is isolated by conventional chromatographic techniques.

For therapeutic administration, the compounds of this invention may be incorporated with excipients and used, for example, in the form of tablets, dragees, capsules, liquids, elixirs, emulsions, suspensions, syrups, chocolate, candy, wafers, chewing gum and the like. Such compositions and preparations should contain at least 0.1% of active ingredient. The percentage in the compositions and preparations may, of course, be varied, and may conveniently be between about 2% and 60% or more of the weight of the unit. The amount of active component in such therapeutically useful compositions or preparations is such that a suitable dosage will be obtained. This dosage can also be obtained by the use of sustained release preparations. Preferred compositions or preparations according to the present invention are prepared so that a dosage unit form contains between about 1 and about 250 mg. of active component.

Tablets, pills, dragees and the like may contain the following: a binder such as gum tragacanth, acadia, corn starch or gelatin; a disintegrating agent such as corn starch, potato starch, alginic acid or the like; a lubricant such as stearic acid, magnesium stearate, talc or the like; a sweetening agent such as sucaryl or saccharin may be added, as well as a flavoring such as peppermint, oil of wintergreen or cherry flavoring.

The compounds of the present invention are active in vivo as inhibitors of platelet aggregation.

The compounds were administered orally to male rats in various concentrations. After one to 2 hours the rats were bled and platelet rich plasma obtained. Collagen was added at a concentration of 500 mcg./ml. to induce platelet aggregation and comparisons were made between control and treated samples. The percent inhibition of aggregation produced by the test compound was recorded. The results of this test on a typical compound of this invention appear in Table I.

TABLE I

| Compound | Dose mg./kg. | % Inhibition |
|---|---|---|
| γ-Hydroxy-4-biphenyl-butyric acid | 50 | 19 |
|  | 25 | 25 |
|  | 10 | 25 |

In a second test the in vivo activity is determined in mice. Active compounds inhibit the respiratory depression associated with platelet aggregation and thrombosis induced by arachidonic acid. Mice were treated orally by gastric lavage with the test compounds in a starch suspension at various dosage levels. Two hours later a challenge dose of arachidonic acid was given to the mice intravenously at a concentration of 50 mg./kg. The period of respiratory distress for each animal was recorded in seconds by observation. The results of a typical compound of this invention appear in Table II in terms of percent inhibition in comparison with controls.

TABLE II

| Compound | Dose mg./kg. | % Inhibition |
|---|---|---|
| γ-Hydroxy-4-biphenyl-butyric acid | 1 | 46 |
|  | 10 | 51 |
|  | 25 | 66 |
|  | 50 | 63 |

The compounds of the present invention are active in vivo as anti-inflammatory agents.

In determining the acute anti-inflammatory activity, Royal Hart, Wistar strain rats ranging in weight from 80 to 90 grams were used. The rats were fasted overnight prior to dosing but had free access to water. The compounds were administered in aqueous suspension, by gavage, in a column of 1.7 ml. per 50 g. of rat [corresponds to the hydration volume used by Winter, et al., Proc. Soc. Exp. Biol. and Med. 111, 544–547 (1962)].

The phlogistic agent used was carrageenin prepared as a sterile 1% suspension in 0.9% aqueous sodium chloride for routine testing. A volume of 0.05 ml. was injected through a 26 gauge needle into the plantar tissue of the right hind paw. Measurements were made 5 hours after drug administration (4 hours after carrageenin challenge).

Volumes of both the normal and carrageenin inflamed feet were determined. The difference between the two measurements is considered to be the increased edema due to the carrageenin administration. Results are expressed as a C/T efficacy ratio (edema of control animals/edema of treated animals) and a C/T ratio of greater than 1.41 is considered active.

The results of this test on a typical compound of this invention is recorded in Table III.

TABLE III

| Compound | Dose mg./kg. | C/T Edema Ratio |
|---|---|---|
| γ-Hydroxy-4-biphenylbutyric acid | 250 | 2.0 |

In a second test the activity against chronic inflammation in adjuvant induced arthritis was determined. Groups of 3 Royal Hart, Wistar strain rats, weighing 200±10 g. each were injected intradermally in the right hind paw with Freund's adjuvant (dried human tubercle bacilli in a mineral oil vehicle) at a dose of 2 mg./kg. of body weight. Test compounds were administered orally in a 1.5% starch vehicle at 50 mg./kg. of body weight once daily on days 0 through 13 post challenge. Control rats were treated in a similar manner, but given only starch vehicle. On the 14th day post challenge the diameter of the injected paw (primary lesion) was measured by micrometer caliper. The volume of inflamed paws was estimated from these measurements and the results are expressed as percent inhibition of swelling as compared to controls. At the same time, the other inflamed sites, such as ears, paws and tail (secondary lesions) were observed and each rat was graded as to the degree of inflammation and swelling present. The grading is based on a scale of 0 to 24, where 0 represents a complete absence of induced arthritic nodules and 24 represents the maximum degree of inflammation. The mean grade for each treated group is calculated and the effects of each compound are expressed as percent inhibition of the control grade. Table IV records the results of this test on a typical compound of this invention.

TABLE IV

| Compound | % Inhibition of Swelling (primary lesion) | % Inhibition of Control grade (secondary lesion) |
|---|---|---|
| γ-Hydroxy-4-biphenylbutyric acid | 51 | 30 |

Another method of determining a drug effect on conditions which result in inflammation is by measuring the effect on ultraviolet induced erythema in guinea pigs. Albino guinea pigs were depilitated on their flanks, the evening before testing, with a standard mixture of barium sulfide and gum acacia. On the morning of the test, groups of 4 guinea pigs were dosed by gavage one hour prior (−1 hour) to ultraviolet exposure. At 0 hour they were restrained in a plastic container which allows exposure of 3 circular spots. They were then exposed to ultraviolet irradiation from a "Hanovia" Kromayer lamp, model 10, for 60 seconds. At one and four hours, the degree of erythema for each of the three sites was assessed according to the following scoring system: 0=no erythema, 0.5=incomplete circle or faint erythema and 1.0=incomplete circle of distinct erythema. Thus, the maximum score for each animal was 3.0. The results of this test on a typical compound of the present invention appears in Table V.

TABLE V

| Compound | Dose mg./kg. | No. of animals | Score (avg.) 1 hour | Score (avg.) 4 hour |
|---|---|---|---|---|
| γ-Hydroxy-4-biphenylbutyric acid | 250 | 8 | 0 | 2.0 |
|  | 125 | 4 | 0.4 | 2.9 |
|  | 62.5 | 4 | 0 | 2.1 |

DETAILED DESCRIPTION OF THE INVENTION

Particular embodiments of this invention are detailed in the following examples.

EXAMPLE 1

γ-Hydroxy-4-biphenylbutyric acid

A 25.4 g. portion of 3-(4-biphenylylcarbonyl)propionic acid is dissolved in 2 liters of water made alkaline with sodium hydroxide. A 37.8 g. portion of sodium borohydride is added and the mixture is stirred for 2 hours. The suspension is then slowly poured into 100 ml. of glacial acetic acid. The mixture is cooled and the resulting solid is filtered, washed with water and dried giving the desired product, m.p. 139°–140° C.

EXAMPLE 2

γ-4'-Dihydroxy-4-biphenylbutyric acid

A 50 g. portion of p-methoxybiphenyl and 30 g. of succinic anhydride are mixed in 600 ml. of nitrobenzene and cooled to about 5° C. A 73 g. portion of aluminum chloride is added in portions keeping the temperature at about 5° C. The mixture is then stirred for 15 hours and allowed to stand at room temperature. The mixture is poured into ice and then steam distilled until no more nitrobenzene comes over. The residue solidifies and is dissolved in 1,250 ml. of water containing 63 g. sodium carbonate. The solution is boiled with charcoal, filtered and the filtrate is chilled. The precipitate is filtered at room temperature and the gummy mixture is acidified with HCl and cooled. The precipitate is triturated with 50% acetic acid and the insoluble portion is recovered by filtration giving 4'-methoxy-γ-oxo-4-biphenylbutyric acid.

A 3.0 g. portion of the preceding product, 20 ml. of glacial acetic acid and 6 ml. of hydrogen bromide is refluxed for 16 hours. The resulting mixture is cooled, diluted with 25 ml. of water and the precipitate is collected by filtration. The material is recrystallized from ethyl alcohol after treatment with activated charcoal. The initial acidic filtrate is evaporated, combined with the recrystallized material and refluxed again with 20 ml. of acetic acid and 6 ml. of hydrogen bromide. The resulting mixture is diluted with a small amount of water, cooled and filtered. The precipitate is collected and recrystallized from ethyl alcohol to give 1.4 g. of 4'-hydroxy-γ-oxo-biphenylbutyric acid.

A 0.54 g. portion of the above product is dissolved in 80 ml. of water and 2.4 ml. of N sodium hydroxide with stirring. To the stirred solution is added 0.76 g. of sodium borohydride. Stirring is continued for 16 hours at room temperature. The resulting clear solution is cooled in ice and 3 ml. of glacial acetic acid is added to give a gelatinous precipitate. The mixture is filtered through diatomaceous earth, and the filtered material is rinsed successively with diethyl ether. The combined ethereal filtrates are dried over magnesium sulfate and evaporated to dryness. The residue is crystallized from ethyl acetate-benzene and the product of the Example (0.3 g.) is collected by filtration and air dried, mp. 141.5°–143.5° C.

EXAMPLE 3

β,γ-Dihydroxy-threo-4-biphenylbutyric acid

To a 10.0 g. portion of 3-(4-biphenylylcarbonyl) propionic acid stirred in one liter of methylene dichloride at room temperature is added 6.8 g. of bromine in 50 ml. of methylene dichloride. Stirring is continued at room temperature for 2½ hours. The solvent is evaporated resulting in 13 g. of β-bromo-γ-oxo-4-biphenylbutyric acid.

To a 12.5 g. portion of the above compound stirred in 100 ml. of water at room temperature is added 50 ml. of N sodium hydroxide, then 1.0 g. of sodium borohydride is added and stirring is continued for 16 hours. The resulting solution is filtered and the pH of the filtrate is adjusted to pH 6 with glacial acetic acid. The solution is extracted twice with chloroform and the combined chloroform extract is rinsed with water, dried over magnesium sulfate and evaporated to an oil. The oil is triturated with ether to yield 0.9 g. of curde cis-5-(4-biphenylyl)dihydro-4-hydroxy-2(3H)-furanone.

A 1.6 g. portion of the crude product (prepared as described above) is recrystallized twice from ethyl alcohol to give 0.8 g. of purified product.

A 0.5 g. amount of the purified material above in 50 ml. of ethyl alcohol and 125 ml. of a 10% aqueous solution of sodium carbonate is heated briefly on a steam bath, then is stirred at room temperature for 16 hours.

The solution is evaporated to a small volume and the reaction mixture is cooled and filtered. The resultant precipitate is stirred at room temperature for 3 hours in 100 ml. of 10% acetic acid and is filtered. The filtered acid is crystallized from ethanol-water yielding off-white crystals. This material is recrystallized from ethyl alcohol after treatment with activated charcoal to yield 180 mg. of the product of the Example as a white solid m.p. 178°–180° C.

EXAMPLE 4

β,γ-Dihydroxy-erythro-4-biphenylbutyric acid

To a solution of 15 g. of -bromo- -oxo-4-biphenylbutyric acid in 800 ml. of water and 25 ml. of N sodium hydroxide, stirred for 10 minutes at room temperature, is added 7.6 g. of sodium borohydride. Stirring is continued for 16 hours and the solution is filtered. The filtrate is poured onto a mixture of 20 ml. of glacial acetic acid and ice with some diethyl ether added to minimize foaming. The aqueous layer is then extracted twice with ether. The combined ether solution is dried over magnesium sulfate and evaporated. The resultant solid is rinsed twice with ether. The rinsings are evaporated to dryness and the residue obtained is combined with the residue which is collected by filtering the previously ether extracted aqueous layer after standing overnight, to yield a total 2.2 g. of material. The preceding material is chromatographed. Fractions 9–17 are collected and evaporated to dryness to give 420 mg. of trans-5-(4-biphenylyl)dihydro-4-hydroxy-2(3H)-furanone.

A 400 mg. portion of the preceding product in 80 ml. of absolute ethyl alcohol and 50 ml. of a 10% aqueous solution of sodium carbonate is stirred at room temperature for 16 hours. The solution is evaporated to dryness and the resulting solid is triturated with water and acetic acid, cooled and filtered. The material is air dried and is twice recrystallized from isopropyl alcohol to yield the product of the example as colorless crystals, m.p. 158°–160° C.

EXAMPLE 5

α,γ-Dihydroxy-erythro-4-biphenylbutyric acid and α,γ-Dihydroxy-threo-4-biphenylbutyric acid A total of 9 guinea pigs are each dosed with 100 ml./kg. of 3-(4-biphenylylcarbonyl)-propionic acid. Their combined 24 hour urinary excretion (230 ml.) is acidified and extracted with chloroform:ether (8:3). The solvent is evaporated under nitrogen and the residue is partitioned on a celite column eluting with heptane:ethyl acetate:methanol:water:acetic acid (300:200:80:20:1.5), resulting in the separation and recovery of the desired threo and erythro compounds.

EXAMPLE 6

Preparation of Compressed Tablets

| Ingredient | mg./Tablet |
|---|---|
| Active compound | 0.5-250 |
| Dibasic Calcium Phosphate NF | qs |
| Starch U.S.P. | 20 |
| Modified Starch | 5 |
| Magnesium stearate U.S.P. | 1-3 |

EXAMPLE 7

Preparation of Hard Shell Capsule

| Ingredient | mg./Capsule |
|---|---|
| Active Compound | 0.5-250 |
| Lactose Spray dried | qs |
| Magnesium stearate | 1-5 |

EXAMPLE 8

Preparation of Oral Suspension

| Ingredient | % W/V |
|---|---|
| Active compound | 0.5-5 |
| Polysorbate 80 U.S.P. | 0.1 |
| Flavoring agent | qs |
| Methylparaben U.S.P. | 0.18 |
| Propylparaben U.S.P. | 0.02 |
| Liquid sugar | 75.0 |
| Purified water qs ad | 100.0 |

These novel compounds possess asymmetric centers and thus can be produced as racemic mixtures or as individual enantiomers. The racemic mixtures can be resolved if desired at appropriate stages by methods known to those skilled in the art, to obtain the respective individual enantiomers. It is to be understood that the racemic mixtures and the individual enantiomers are encompassed within the scope of the present invention.

Other embodiments of this invention will be obvious to those skilled in the art without departing from the spirit of the invention. The foregoing examples are merely illustrative of the invention which is limited solely by the claims.

I claim:

1. A compound selected from those of the formula:

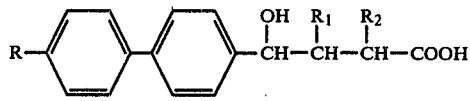

wherein R, $R_1$ and $R_2$ are each selected from the group consisting of hydrogen and hydroxy with the proviso that when R is hydrogen, then $R_1$ and $R_2$ cannot both be hydrogen.

2. The compound according to claim 1, $\gamma,4'$-Dihydroxy-4-biphenylbutyric acid.

3. The compound according to claim 1, $\beta,\gamma$-Dihydroxy-threo-4-biphenylbutyric acid.

4. The compound according to claim 1, $\beta,\gamma$-Dihydroxy-erythro-4-biphenylbutyric acid.

5. The compound according to claim 1, $\alpha,\gamma$-Dihydroxy-erythro-4-biphenylbutyric acid.

6. The compound according to claim 1, $\alpha,\gamma$-Dihydroxy-threo-4-biphenylbutyric acid.

7. A process for producing compounds of the formula:

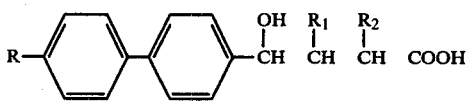

wherein R, $R_1$ and $R_2$ are each selected from the group consisting of hydrogen and hydroxy, which comprises treating 3-(4-biphenylylcarbonyl)propionic acid with bromine in methylene chloride, treating the $\beta$-bromo-$\nu$-oxo-4-biphenylbutyric acid so produced with sodium borohydride in alkaline solution followed by acidification, giving the cis or trans-5-(4-biphenylyl)dihydro-4-hydroxy-2(3H)-furanone which is then treated with base to produce the desired product.

* * * * *